United States Patent [19]

Lambert et al.

[11] Patent Number: 4,544,743

[45] Date of Patent: Oct. 1, 1985

[54] SALTS OF 1,3,5-OXADIAZINES-2,4,6-TRIONES, 1,3,5-OXADIAZINES-2,4,6-TRIONES AND THE PREPARATION THEREOF

[75] Inventors: Pierre M. Lambert, Louvain-la-Neuve; Ignacio De Aguirre-Otegui, Wavre-Limal, both of Belgium

[73] Assignee: Societe Carbochimique, Brussels, Belgium

[21] Appl. No.: 507,637

[22] Filed: Jun. 27, 1983

[30] Foreign Application Priority Data

Jun. 29, 1982 [LU] Luxembourg .......................... 84242

[51] Int. Cl.$^4$ ........................................... C07D 273/04
[52] U.S. Cl. ........................................ 544/64; 544/67
[58] Field of Search ...................... 544/67, 64

[56] References Cited

U.S. PATENT DOCUMENTS 3,748,329 7/1973 Liebsch et al. ........................ 544/67
4,443,597 4/1984 Kamatani et al. ..................... 544/67

FOREIGN PATENT DOCUMENTS 138206 10/1979 German Democratic Rep. ... 544/67

*Primary Examiner*—John M. Ford
*Attorney, Agent, or Firm*—Sughrue, Mion, Zinn, Macpeak and Seas

[57] ABSTRACT

This invention relates to new salts of 1,3,5-oxadiazines-2,4,6-triones, to new 1,3,5-oxadiazines-2,4,6-triones and to the preparation thereof.

33 Claims, No Drawings

SALTS OF 1,3,5-OXADIAZINES-2,4,6-TRIONES, 1,3,5-OXADIAZINES-2,4,6-TRIONES AND THE PREPARATION THEREOF

SUMMARY OF THE INVENTION

The new salts of 1,3,5-oxadiazines-2,4,6-triones according to this invention, which may also be called 1,3,5-oxadiazinates-2,4,6-triones, are represented by the following general formula (I):

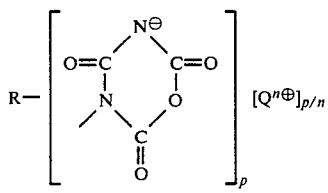
(I)

in which
R represents a substituted or unsubstituted, mono- or polyvalent hydrocarbon radical;
Q represents a metal or a group containing a number n of ammonium, phosphonium or arsonium functions, which may be unsubstituted or mono-, di-, tri- or tetrasubstituted;
p is an integer which is at least equal to 1;
n represents the oxidation number of the metal or the number of ammonium, phosphonium or arsonium functions present in the Q group.

The new asymmetrical molecular 1,3,5-oxadiazines-2,4,6-triones according to this invention may be represented by the following general formula (II):

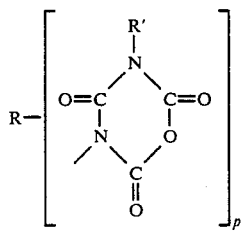
(II)

in which R and p have the same meaning as in the compounds of general formula (I) and R', which is different from R, represents a possibly substituted hydrocarbon radical, hydrogen, a halogen or a chlorocarbonyl, carbamoyl, sulfamoyl or sulfonyl radical.

This invention also relates to processes for the preparation of the new compounds of formulae (I) and (II).

The salts of 1,3,5-oxadiazines-2,4,6-triones of the formula (I) are prepared by reacting an isocyanate or polyisocyanate of the formula:

$$R(NCO)_p \qquad (III)$$

in which R and p have the above meanings with a cyanate salt of the formula:

$$Q(NCO)_n \qquad (IV)$$

in which Q represents a metal or a group containing unsubstituted or mono-, bi-, tri- or tetrasubstituted ammonium, phosphonium or arsonium functions and n has the above meaning, and with carbon dioxide.

The symmetrical or asymmetrical (formula II) molecular 1,3,5-oxadiazines-2,4,6-triones are prepared by reacting a compound of the formula (I) with a compound of the formula:

$$R'Y \qquad (IX)$$

in which R' represents a monovalent or polyvalent aliphatic, cycloaliphatic, arylaliphatic or heterocyclic radical which may be substituted or hydrogen, a halogen or a chlorocarbonyl, carbamoyl, sulfamoyl or sulfonyl radical and Y represents a halogen, a sulfate radical, a rest of a mineral or organic acid, an alkoxy radical or an amide radical.

THE PRIOR ART

In respect of the molecular 1,3,5-oxadiazines-2,4,6-triones, it is known, from K. H. Slotta and R. Tschesche, Ber., 60, 295 (1927) and from A. Etienne and B. Bonte, Bull. Soc. Chim. France 7-8, 1497 (1974), to prepare symmetrical disubstituted molcular 1,3,5-oxadiazine-2,4,6-triones of the following general formula:

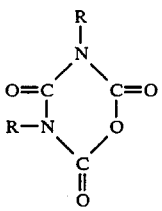

in which the substituents carried by the nitrogen atoms in the 3 and 5 positions are identical, from two molecules of an aliphatic isocyanate of the formula RNCO and from carbon dioxide, in the presence of a trialkylphosphine as catalyst. Moreover, the French Pat. No. 1 509 843 (1967)and the West German Pat. No. 1 670 666 (1966) disclose the preparation, by a similar method, of molecular 1,3,5-oxadiazines triones carrying free isocyanate groups, by reacting carbon dioxide with aliphatic diisocyanates.

This type of process has several drawbacks, namely the use of toxic phosphorus derivatives as catalysts and the need of using, for preparing one mole of oxadiazine, two moles of an aliphatic isocyanate which is an expensive reagent.

On the other hand, the asymmetrical 1,3,5-oxadiazines-2,4,6-triones of the formula (II), which carry different substituents in the 3 and 5 positions, are new compounds. The preparation of these asymmetrical 1,3,5-oxadiazines-2,4,6-triones by reacting isocyanates and carbon dioxide gives necessarily a mixture of oxadiazines which are very difficult to separate from each other.

The process according to this invention does not have the above drawbacks. This process allows to prepare easily a multiplicity of molecular 1,3,5-oxadiazines-2,4,6-triones carrying identical or different substituents in the 3 and 5 positions of the heterocyclic ring, under economical conditions.

On the other hand, the salts of 1,3,5-oxadiazines-2,4,6-triones of the formula (I) according to this invention are new compounds, since the preparation of these compounds has still not been described in the literature.

BRIEF DESCRIPTION OF THE INVENTION

This invention relates to new salts of 1,3,5-oxadiazines-2,4,6-triones which may be represented by the following general formula (I):

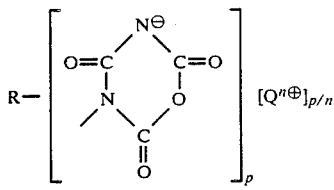

in which
R represents an unsubstituted or substituted, mono- or polyvalent hydrocarbon radical;
Q represents a metal or a group containing a number n of unsubstituted or mono-, di-, tri- or tetrasubstituted ammonium, phosphonium or arsonium functions;
p is an integer equal to at least 1;
n represents the oxidation number of the metal or the number of ammonium, phosphonium or arsonium functions present in the Q group.

This invention also relates to asymmetrical molecular 1,3,5-oxadiazines-2,4,6-triones of the following general formula (II):

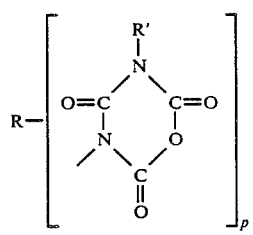

in which R and p have the above meaning and R', which is different from R, represents a possibly substituted hydrocarbon radical, hydrogen, a halogen or a chlorocarbonyl, carbamoyl, sulfamoyl or sulfonyl radical.

The compounds according to this invention may be used for various purposes and are useful as intermediates for the preparation of pharmaceutical products, of selective herbicides and of disinfectants. They may also be used as additives in the manufacture of polymers, particularly of polyurethanes, in which they contribute to the formation of allophanate links and the production of gaseous carbon dioxide useful for forming foams.

These applications are illustrated by the following reactions for preparing allophanates, biurets and ureines from a salt of 3-methyl-1,3,5-oxadiazine-2,4,6-trione and from allyl chloride:

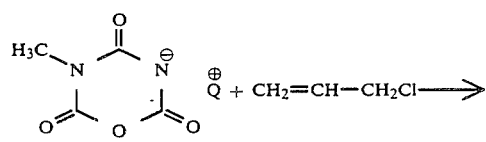

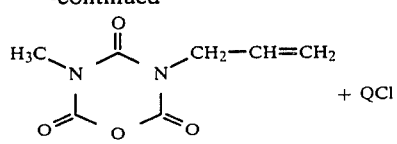

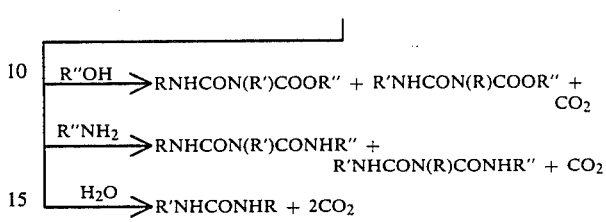

| R"OH | $\rightarrow$ RNHCON(R')COOR" + R'NHCON(R)COOR" + $CO_2$ |
| R"NH$_2$ | $\rightarrow$ RNHCON(R')CONHR" + R'NHCON(R)CONHR" + $CO_2$ |
| H$_2$O | $\rightarrow$ R'NHCONHR + $2CO_2$ |

In these reactions, R represents a methyl radical ($CH_3$), R' an allyl radical ($CH_2CH=CH_2$) and R" is a phenyl radical ($C_6H_5$).

Among the biurets, allophanates and ureines which may be obtained from the compounds according to this invention, some have interesting selective herbicidal properties.

This invention also relates to processes for preparing the new salts of 1,3,5-oxadiazines-2,4,6-triones of the formula (I).

The process for preparing the new compounds of formula (I) is based on the reaction of organic isocyanates with a cyanate salt, in the presence of carbon dioxide. It has surprisingly been found that when these reagents are reacted under particular conditions, it is possible to obtain salts of 1,3,5-oxadiazines-2,4,6-triones, instead of molecular isocyanurates or 1,3,5-oxadiazines-triones. From said salts of 1,3,5-oxadiazines-2,4,6-triones, it is very easy to prepare molecular, mono- or disubstituted, symmetrical or asymmetrical 1,3,5-oxadiazines-2,4,6-triones, the asymmetrical compounds being those represented by the formula (II). These compounds are obtained according to this invention with very good yields, from unexpensive reagents and under economical conditions.

The salts of 1,3,5-oxadiazines-2,4,6-triones of the formula (I) according to this invention are obtained by reacting an isocyanate or polyisocyanate of the formula $$R(NCO)_p \tag{III}$$

in which R and p have the above meanings with a cyanate salt of the formula $$Q(NCO)_n \tag{IV}$$

in which Q represents a metal or a group containing unsubstituted or mono-, bi-, tri- or tetrasubstituted ammonium, phosphonium or arsonium functions and n has the above meaning, and with carbon dioxide.

The reaction A for obtaining the new compounds of the general formula (I) is as follows:

$$R(NCO)_p + pCO_2 + p/_nQ(NCO)_n \longrightarrow \tag{A}$$

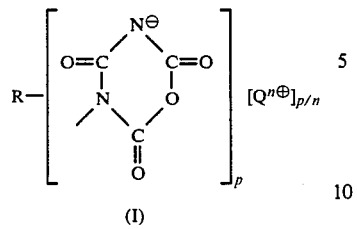

(I)

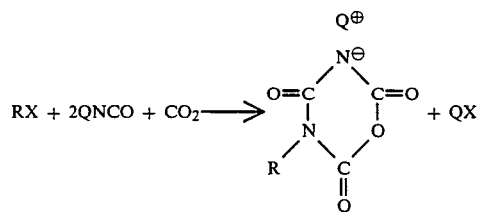

wherein R, Q, p and n have the above meanings.

In the particular case of preparing salts of 1,3,5-oxadiazines-2,4,6-triones of the formula (I) in which $n=1$ and $p=1$, the process according to this invention involves the following reaction B:

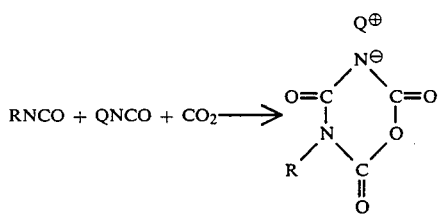

The process A may be possibly carried out in the presence of an organic solvent which does not interfere with the reaction, at temperatures comprised between about $-80°$ C. and $+250°$ C. and under pressures comprised between about 0.2 bar and 150 bars.

In the process A according to the invention, the organic isocyanate of the formula $R(NCO)_p$ may be introduced as such in the reaction mixture or may be prepared by any known method in the solvent used for preparing the salts of 1,3,5-oxadiazines-2,4,6-triones. This combination of the preparation of the isocyanate and of the conversion of this isocyanate, in the same solvent, into salts of 1,3,5-oxadiazines-2,4,6-triones makes the process even more economical, since it does not use an organic isocyanate which is an expensive reagent, as starting material.

The organic isocyanate may particularly be prepared from a cyanate salt and from an organic halide or sulfate, possibly in the presence of a catalyst, as shown by the following reaction C:

RX+QNCO→RNCO+QX    (C)

in which X represents a halogen or a sulfate, alkylsulfate or arylsulfonyl radical.

The direct preparation of salts of 1,3,5-oxadiazines-2,4,6-triones from a cyanate salt, an organic halide or sulfate and carbon dioxide is represented by the following reaction D:

in which R and X have the above meanings.

The starting materials for preparing, in accordance with this invention (reaction A), the salts of 1,3,5-oxadiazines-2,4,6-triones by reacting an organic isocyanate with a cyanate salt and with carbon dioxide are as follows:

a. The organic isocyanates of the following general formula $R(NCO)_p$ are primary, secondary or tertiary aliphatic, cycloaliphatic, arylaliphatic or heterocyclic mono- or polyisocyanates which may possibly be substituted. The preferred organic isocyanates are those in which the nitrogen of the isocyanate function is not directly linked to a carbon atom of an aromatic ring. The preferred organic isocyanates are the methyl isocyanate, the ethyl isocyanate, the 1-isocyanatobutane, the 1-isocyanatodecane, the allyl isocyanate, the 1-isocyanatooctadec-9-ene, the hexamethylene diisocyanate, the 1,4-diisocyanatobut-2-ene, the vinyl isocyanate, the isopropyl isocyanate, the 2,5-diisocyanatohexane, the isocyanato-isoheptadecane, the t-butyl isocyanate, the 5-methyl-2,5,8-triisocyanatononane, the cyclohexyl isocyanate, the 1,3-diisocyanatocyclobutane, the 1,4-diisocyanatocyclohexane, the benzyl isocyanate, the α,α'-diisocyanato-p-xylene, the 3-isocyanatofurane or mixtures of at least two of these compounds.

b. The cyanate salts of the following general formula $Q(NCO)_n$ are cyanates of mono-, bi- or trivalent metals or unsubstituted or mono-, bi-, tri- or tetrasubstituted ammonium, phosphonium or arsonium cyanates. In these cyanates of ammonium, phosphonium or arsonium, Q represents either a radical of the formula:

$(R^I R^{II} R^{III} Z)_n R^{IV}$    (V)

in which n has the above meaning, Z represents nitrogen, phosphorus or arsenic and $R^I$, $R^{II}$, $R^{III}$ and $R^{IV}$, which are identical or different, represent hydrogen or unsubstituted or substituted alkyl, aryl, arylalkyl or heterocyclic radicals; $R^I$ and $R^{II}$ may form together a bivalent radical; or a radical of the formula:

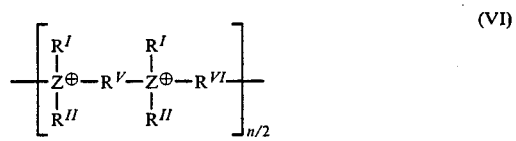

in which Z, $R^I$ and $R^{II}$ have the above meanings, $R^V$ and $R^{VI}$ are bivalent radicals and n has the above meaning.

The preferred cyanate salt depends on the reactivity of the system, of the temperature and of the liquid in which the desired compound is prepared.

In most cases, it is preferable to use a cyanate salt consisting of a cyanate of an alkaline or alkaline-earth metal, most preferably the sodium or potassium cyanates or tetrasubstituted ammonium, phosphonium or arsonium cyanates or mixtures thereof.

The ammonium, phosphonium or arsonium cyanates may possibly be produced in the reaction solvent, prior or during the preparation, by any known method.

Examples of tetrasubstituted ammonium, phosphonium and arsonium cyanates which may be used in the process according to this invention are the tetramethylammonium cyanate, the tetraethylammonium cyanate, the tetrapropylammonium cyanate, the tetrabutylammonium cyanate, the tetraamylammonium cyanate, the tetrahexylammonium cyanate, the tributylmethylammonium cyanate, the tricaprylmethylammonium cyanate, the dodecyltrimethylammonium cyanate, the benzyltrimethylammonium cyanate, the benzyltriethylammonium cyanate, the benzylisopropyldimethylammonium cyanate, the benzyltripropylammonium cyanate, the benzyltributylammonium cyanate, the phenyltrimethylammonium cyanate, the phenyltriethylammonium cyanate, the methyltributylphosphonium cyanate, the tetrabutylphosphonium cyanate, the tetraphenylphosphonium cyanate, the benzyltriethylarsonium cyanate, the tetrapropylarsonium cyanate, the tetraphenylarsonium cyanate, the dimethylpiperidinium cyanate, the methylpyridinium cyanate and the mixtures as well as the substituted derivatives of these compounds.

Other cyanates which may be used in the process according to this invention are the 1,4-bis(trimethylammonium)butane cyanate, the 1,6-bis(triethylammonium)hexane cyanate, the 1,4-dimethyl-1,4-diaza-2,2,2-bicyclo-octane cyanate, the cyanates fixed on an anionic resin of the AMBERLITE IRA 400 (FLUKA) type, the ionene of the formula:

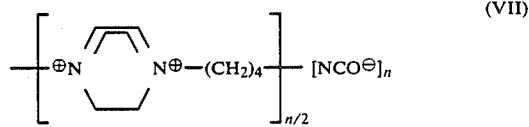

(VII)

and the ionene of the formula:

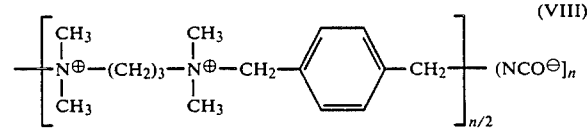

(VIII)

wherein in is comprised between 5 and 40, and the mixtures of these compounds.

c. The carbon dioxide used in the process according to this invention may not contain impurities which interfere with the reaction. However, this carbon dioxide may possibly be diluted by inert substances.

d. The use of catalysts is not essential in the process according to this invention which allows the preparation of the desired compounds with good yields within short periods of time. However, catalysts such as $CaCl_2$ and $MgO$ may be used in specific cases.

The materials, such as the cyanates, which are used in solid form should preferably be in the most possible divided form.

The reaction conditions, such as the temperature, the pressure and the solvent in which the reactions take place, as well as the quantitative proportions of the reagents depend more or less from each other and are selected according to the used reagents and according to the nature of the desired product.

The quantitative proportion of cyanate salt with respect to the organic isocyanate and to the carbon dioxide may be selected within broad limits. This proportion may be stoechiometric or may be higher or lower than the stoechiometric proportion. Generally, 0.5 to 2 equivalents of organic isocyanate, preferably 0.8 to 1.2 equivalents of organic isocyanate are used, per equivalent of cyanate salt.

The amount of carbon dioxide to be used is comprised between 0.1 and 20 moles per equivalent of used cyanate salt and, preferably, between 0.8 and 2 moles.

Although the process according to this invention may be carried out in the absence of any solvent, it is preferred to use an inert organic solvent which does not interfere with the reaction. It is possible to use non-polar organic solvents as well as polar organic solvents. Examples of solvents which may be used in the process according to this invention are the carbon tetrachloride, the chloroform, the dichloromethane, the 1,2-dichlorethane, the 1,1-dichlorethane, the mixture of cis and trans isomers of the 1,2-dichlorethylene, the o-dichlorobenzene, the dioxane, the ethyl acetate, the dimethoxyethane, the tetrahydrofurane, the toluene, the α-methylnaphthalene, the acetone, the methylethylketone, the acetonitrile, the propionitrile, the benzonitrile, the benzyl cyanide, the nitrobenzene, the nitrotoluene, the dimethylformamide, the dimethylacetamide, the tetramethylurea, the N-methylpyrrolidone, the hexamethylphosphotriamide, the dimethyl sulfoxide, as well as mixtures of these solvents. The preferred solvents are the chlorinated hydrocarbons, the linear or cyclic ethers, the ketones and the nitriles.

The proportion of the solvent depends namely of the type of solvent and of the quantitative proportions of the other substances. Generally, it is possible to use up to 50 parts by weight of solvent for each part by weight of reagents. In most cases, it is preferred to use 0.2 to 25 parts by weight of solvent, preferably 1 to 10 parts by weight of solvent, for 1 part by weight of reagents.

The salts of 1,3,5-oxadiazines-2,4,6-triones according to the invention may be prepared at temperatures comprised between −80° C. and +250° C. In most cases, temperatures comprised between −20° C. and 150° C. and particularly temperatures comprised between 0° C. and 70° C. may be used.

The pressure of the carbon dioxide in the reactor is not a limiting factor, provided that the liquid contains dissolved carbon dioxide. For this purpose, the partial pressure of the carbon dioxide in the reactor should preferably be comprised between 0.2 bar and 150 bars, more preferably between 1 and 60 bars. The reactor may also contain an inert gas, such as nitrogen or argon.

The reagents and the solvent may be used in different ways. The reagents and the solvent may particularly be introduced into the reactor at the same time, successively and/or progressively. For example, the total amount of useful carbon dioxide may be introduced into the reactor from the start or during the reaction.

The duration of the reaction varies namely in accordance with the reactivity of the reagents, the temperature, the nature of the solvent and the possible presence of catalysts. Generally, the duration of the reaction is comprised between 0.5 second and 24 hours and, in most cases, between 1 second and 10 hours.

The yields of salts of 1,3,5-oxadiazines-2,4,6-triones prepared by the process according to the invention are generally high and may be of more than 90% after 1 minute of reaction at 25° C. and under a pressure of 1 bar.

The conversion of the salts of 1,3,5-oxadiazines-2,4,6-triones into molecular symmetrical or asymmetrical (formula II) 1,3,5-oxadiazines-2,4,6-triones is carried out, according to this invention, by reacting a compound of the formula (I) with a compound of the formula

R'Y    (IX)

in which R' represents a monovalent or polyvalent aliphatic, cycloaliphatic, arylaliphatic or heterocyclic radical which may be substituted, or hydrogen, a halogen or a chlorocarbonyl, carbamoyl, sulfamoyl or sulfonyl radical and Y represents a halogen, a sulfate radical, a rest of a mineral or organic acid, an alkoxy radical or an amide radical.

Thus, in accordance with this invention, it is possible to obtain from salts of 1,3,5-oxadiazines-2,4,6-triones of the general formula (I), molecular 1,3,5-oxadiazines-2,4,6-triones of the general formula (II) by the following reaction E:

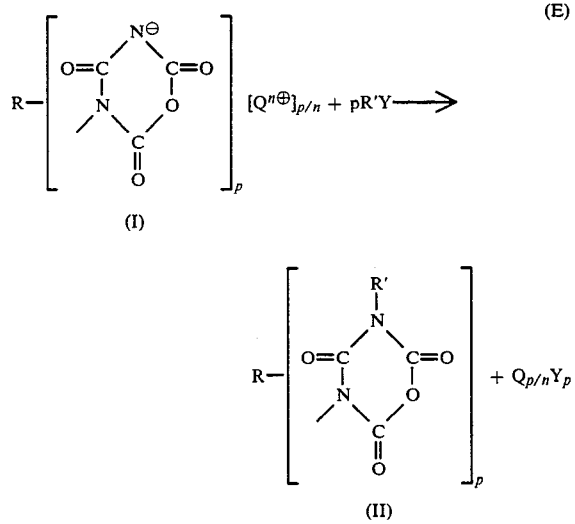

in which
R represents a monovalent or polyvalent aliphatic, cycloaliphatic, arylaliphatic or heterocyclic radical which may be substituted;
Q represents a metal or a group containing unsubstituted or mono-, bi-, tri- or tetrasubstituted ammonium, phosphonium or arsonium functions;
p is an integer equal to or having a value of more than 1;
n represents the oxidation number of the metal or the number of ammonium, phosphonium or arsonium functions present in the Q group;
R' represents a monovalent or polyvalent aliphatic, cycloaliphatic, arylaliphatic or heterocyclic radical which may be substituted, or hydrogen, a halogen or a chlorocarbonyl, carbamoyl, sulfamoyl or sulfonyl radical, and Y represents a halogen, a sulfate radical, a rest of a mineral or organic acid, an alkoxy radical or an amide radical.

Molecular monosubstituted or disubstituted, symmetrical or asymmetrical 1,3,5-oxadiazines-2,4,6-triones may be prepared by reaction E. The asymmetrical monosubstituted or disubstituted compounds are new and are compounds within the scope of this invention.

When an acid is used as a reagent of the general formula R'Y, monosubstituted oxadiazines having the following formula (X) are obtained:

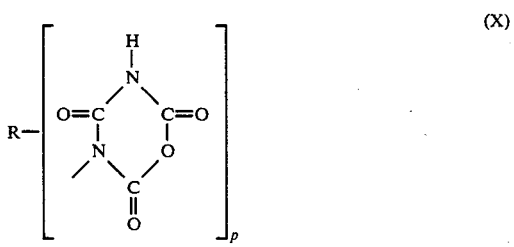

It is possible to use any organic or mineral acid capable of ceding a proton to the salts of 1,3,5-oxadiazines-2,4,6-triones which have basic properties. For example, an acid selected from hydrochloric acid, sulfuric acid, acetic acid, benzoic acid, formic acid and oxalic acid may be used. The neutralization may be carried out in the organic solvent of the reaction medium, in water, in another solvent or in a mixture of solvents.

For preparing disubstituted symmetrical or asymmetrical 1,3,5-oxadiazines-2,4,6-triones of the general formula (II), it is preferred to use, as reagents of the general formula R'Y, organic halides or sulfates containing 1 to 30 carbon atoms, preferably 1 to 18 carbon atoms, these reagents being possibly substituted by radicals which do not interfere with the reaction.

Examples of organic halides and sulfates which may be used in the process according to the invention are the dimethyl sulfate, the diethyl sulfate, the benzyl chloride, the allyl chloride, the 1-chlorobut-2-ene, the cyclohexyl chloride, the methyl chloride, the methyl iodide, the α-chloro-p-nitrotoluene, the 1-chlorohexane, the α-chloro-p-trifluoromethyltoluene, the acetyl chloride, the benzoyl chloride, the p-toluenesulfonyl chloride, the oxalyl chloride, the phthalyl chlorides, the 1,4-dichlorobutene, the α, α'-dichloro-m-xylene, the α, α'-dichloro-p-xylene, the 1,6-dichlorohexane or the mixtures and the substituted derivatives of these compounds.

According to an embodiment of the process of the invention (reaction E), the molecular disubstituted symmetrical or asymmetrical 1,3,5-oxadiazines-2,4,6-triones may be obtained directly by reacting an organic isocyanate, a cyanate salt, carbon dioxide and the reagent of the general formula R'Y.

This embodiment is represented by the following reaction F:

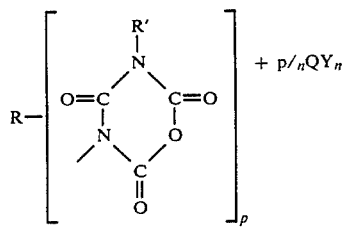

The isocyanate of the formula $R(NCO)_p$ used in this reaction may be introduced as such in the reaction mixture.

According to another feature of the invention, it is also possible to prepare the isocyanate of the formula $R(NCO)_p$ in the reaction mixture itself, from the cyanate of formula QNCO and from an organic halide or sulfate of the formula $RX_p$.

By reacting the cyanate of the formula QNCO, the organic halides or sulfates of the formulae RX and R'Y and carbon dioxide, it is thus possible to combine, in a single reaction mixture, the reactions for the preparation of the isocyanate, for the conversion of the isocyanate into salts of 1,3,5-oxadiazines-2,4,6-triones and for the conversion of the latter into molecular disubstituted symmetrical or asymmetrical 1,3,5-oxadiazines-2,4,6-triones. This preparation is shown by the following reaction G:

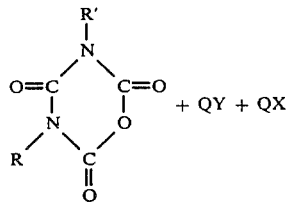

EXAMPLES

The following examples illustrate the present invention.

The processes described in these examples have been carried out in a discontinuous manner in Grignard-type reactors. It is obvious that reactors working in a continuous manner may also be used.

The obtained compounds have been identified by determination of their elementary compositions, potentiometric titration, infrared spectroscopy analysis, nuclear magnetic resonance of $^{13}C$ and mass spectroscopy.

EXAMPLE 1

A glass reactor of 0.5 liter has been used. This reactor is provided with 5 openings equipped with a magnetic stirrer, a reflux condenser, a thermometer, a device for introducing a liquid and a device for introducing a gas through a diffuser immerged in the reaction mixture. The temperature is controlled by means of a thermostat.

22.4 g of tetrapropylammonium cyanate (0.10 mole) and 250 ml of anhydrous dichloromethane are introduced into the reactor. This solution is maintained saturated with carbon dioxide. After the reagents have been dissolved, 5.7 g of methyl isocyanate (0.1 mole) are added to the stirred mixture at a temperature of 25° C. After 2 minutes of reaction, the solvent is distilled under vacuum. After washing with carbon tetrachloride, 27.6 g of tetrapropylammonium 3-methyl-1,3,5-oxadiazinate-2,4,6-trione (yield: 85%) of the formula (I) are obtained.

EXAMPLE 2

The process disclosed in example 1 is used, except that the solvent is not distilled. 15.1 g of methyl sulfate (0.12 mole) are added to the solution of 3-methyl-1,3,5-oxadiazine-2,4,6-trione. The solvent is evaporated after 10 minutes of reaction at a temperature of 25° C. After washing with water and carbon tetrachloride, 14.6 g of 3,5-dimethyl-1,3,5-oxadiazine-2,4,6-trione (yield: 92%) which is a symmetrical disubstituted 1,3,5-oxadiazine trione are obtained.

EXAMPLE 3

The process described in example 1 is carried out. 15.2 g of benzyl chloride (0.12 mole) are added to the obtained solution of the salt of 3-methyl-1,3,5-oxadiazine-2,4,6-trione. After 3 hours of reaction at a temperature of 60° C., one obtains 19.4 g of 3-methyl-5-benzyl-1,3,5oxadiazine-2,4,6-trione (yield: 83%) which is an asymmetrical disubstituted 1,3,5-oxadiazine trione of the formula (III).

EXAMPLE 4

34.1 g of tetraamylammonium cyanate (0.1 mole) and 250 ml of anhydrous tetrahydrofurane are introduced into the reactor described in example 1. This solution is maintained saturated with carbon dioxide. 7.1 g of ethyl isocyanate (0.1 mole) are progressively added, during 5 minutes, to the stirred reaction mixture maintained at 25° C. The solvent is evaporated after 10 minutes of reaction at 25° C. The product is washed with ether and 41 g of tetraamylammonium 3-ethyl-1,3,5-oxadiazinate-2,4,6-trione (yield: 90%) of the formula (I) are obtained.

EXAMPLE 5

9.4 g of acetyl chloride (0.12 mole) are added to the solution of the oxadiazine salt obtained in example 4. After distillation under vacuum, the solid is washed with carbon tetrachloride. 17 g of 3-methyl-5-acetyl-1,3,5-oxadiazine-2,4,6-trione (yield: 85%) of the formula (II) are obtained.

EXAMPLE 6

24.3 g of finely divided potassium cyanate (0.3 mole), 5.7 g of $CH_3NCO$ (0.1 mole) and 250 ml of anhydrous acetonitrile are introduced into a reactor of 0.5 liter in stainless steel, provided with a stirrer and with a device for introducing a gas and a liquid. The pressure of carbon dioxide is maintained constant at 15 bars in the reactor. The reaction is carried out during 6 hours, while stirring the reaction mixture, at a temperature of 70° C. The hot solution is then filtered and the filtrate is distilled under vacuum. By treating the obtained solid with water, the potassium 3-methyl-1,3,5-oxadiazinate-2,4,6-trione which is soluble in water, is separated from the trimethylisocyanurate which is insoluble in water. 6.4 g of potassium 3-methyloxadiazinate (yield: 35%) of the formula (I) are obtained.

In another test carried out under the same conditions, the aqueous solution containing the potassium 3-methyloxadiazinate has been neutralized with hydrochloric acid. 4.3 g of 3-methyl-1,3,5-oxadiazine-2,4,6-trione (yield: 30%) of the formula (II) are obtained.

EXAMPLE 7

34.6 g of tetraamylammonium cyanate (0.1 mole) and 250 ml of tetrahydrofurane are introduced into the reactor described in example 1. The solution is maintained saturated with $CO_2$ at the atmospheric pressure. 8.4 g of hexamethylene diisocyanate (0.05 mole) are progressively added during 5 minutes. After 10 minutes of reaction, the solvent is evaporated and the obtained solid is washed with carbon tetrachloride. 44 g (yield: 94%) of tetraamylammonium bis-oxadiazinate of the following formula are obtained:

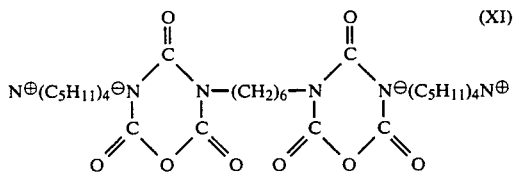

(XI)

this compound having a structure corresponding to that of formula (I).

In another test carried out in the same manner, 0.12 mole of dimethylsulfate are added to the solution of bis-oxadiazinate. After 10 minutes of reaction at 25° C., the solution is distilled under vacuum. The solid residue is washed with water and with carbon tetrachloride. 16.6 g (yield: 90%) of the bis-oxadiazine of the formula:

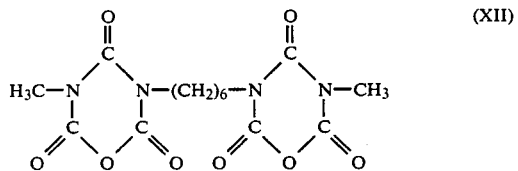

(XII)

are obtained.

EXAMPLE 8

This example illustrates the possibility of combining the production of the organic isocyanates with the preparation of the 1,3,5-oxadiazines-2,4,6-triones.

56.9 g of tetrabutylammonium cyanate (0.2 mole) and 200 ml of acetonitrile are introduced into the reactor described in example 1. The solution is saturated with $CO_2$ under a pressure of 1 bar at a temperature of 25° C. 0.09 mole of methyl sulfate dissolved in 50 ml of acetonitrile is progressively introduced at a constant flow rate into the stirred reaction mixture during 10 minutes. After 10 minutes of additional reaction, the disappearing of the total amount of used methyl sulfate is checked and the amount of remaining cyanate salt is determined. In this example, the solution still contains at this time 0.02 mole of cyanate salt. The solution is treated as described in example 1. 21.2 g of tetrabutylammonium 3-methyl-1,3,5-oxadiazinate-2,4,6-trione of the formula (I) are obtained.

EXAMPLE 9

The same reagents and the same operating conditions as in example 8 are used. Thereafter, 0.12 mole of benzyl bromide are added to the solution obtained in example 8. The reaction mixture is stirred during 2 hours at 50° C. 11.5 g of 3-methyl-5-benzyl-1,3,5-oxadiazine-2,4,6-trione of the formula (II) are obtained.

EXAMPLE 10

6 g of finely divided potassium cyanate and 250 ml of dimethylsulfoxide are introduced into the reactor described in example 1. The obtained suspension is saturated with carbon dioxide. After introduction of 0.08 mole of methyl isocyanate into the stirred reaction mixture at a temperature of 25° C., this reaction mixture is still maintained saturated with $CO_2$. After 5 minutes of reaction at 25° C., 11 g (yield: 85%) of potassium 3-methyl-1,3,5-oxadiaziinate-2,4,6-trione of the formula (I) are obtained.

EXAMPLE 11

0.1 mole of tetraphenylarsonium cyanate and 250 ml of dichloromethane are introduced into the reactor described in example 1. After saturation with carbon dioxide, 0.1 mole of benzyl isocyanate is progressively added. The reaction mixture is stirred during 10 minutes at 50° C. One obtains tetraphenylarsonium 3-benzyl-1,3,5-oxadiazinate-2,4,6-trione of the formula (I) with a yield of 37%.

EXAMPLE 12

30 g of tributylbenzylammonium cyanate (0.094 mole) and 100 ml of anhydrous tetrahydrofurane are introduced into the reactor described in example 1. The solution is maintained saturated with carbon dioxide and 8.3 ml of ethyl isocyanate (0.105 mole) are progressively added (during 1 minute) to the stirred solution at a temperature of 25° C. The tributylbenzylammonium cyanate disappears after 5 minutes of reaction at 25° C. 36 g of tributylbenzylammonium 3-ethyl-1,3,5-oxadiazinate-2,4,6-trione of the formula (I) are obtained.

EXAMPLE 13

The process described in example 12 is carried out and 11.5 ml of ethyl bromoacetate (0.104 mole) are then added to the solution of the oxadiazine salt. After distillation of the solvent under vacuum, the obtained solid is washed with water and with carbon tetrachloride. 17.3 g of 3-ethyl-5-ethylaceto-1,3,5-oxadiazine-2,4,6-trione of the formula (II) are obtained.

EXAMPLE 14

165 g of tributylbenzylammonium cyanate (0.518 mole) and 500 ml of anhydrous tetrahydrofurane are introduced in a reactor similar to the reactor described in example 1, except that the volume of this reactor is of 1 liter. The solution is saturated with carbon dioxide and 65 ml of butyl isocyanate (0.577 mole) are added to the stirred mixture at a temperature of 25° C. After 5 minutes of reaction, the solvent is distilled under vacuum. The solid residue is washed with carbon tetrachloride. 215 g of tributylbenzylammonium 3-butyl-1,3,5-oxadiazinate-2,4,6-trione (yield: 90%) of the formula (I) are obtained.

EXAMPLE 15

The process described in example 14 is carried out without distillation of the solvent. 72 g of methyl sulfate (0.57 mole) are added to the solution of the salt of tributylbenzylammonium 3-butyl-1,3,5-oxadiazine-2,4,6-trione. The solvent is evaporated after 5 hours of reaction at 25° C. The solid residue is washed with water and with carbon tetrachloride. 88 g of 3-butyl-5-methyl- 1,3,5-oxadiazine-2,4,6-trione (yield: 81%) of the formula (II) are obtained.

We claim:

1. A 1,3,5-oxadiazine-2,4,6-trione salt of the following formula (I):

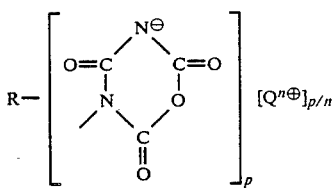 (I)

in which
- R represents a monovalent, divalent or trivalent alkyl, alkylene, cycloalkyl or arylalkyl radical containing at most 18 carbon atoms;
- Q represents a mono-, bi- or trivalent metal or a group containing a number n of unsubstituted or mono-, di-, tri-, or tetrasubstituted ammonium, phosphonium or arsonium radicals selected from the group consisting of the radicals of the formulae:

$(R^I R^{II} R^{III} Z)_n R^{14}$, and (V)

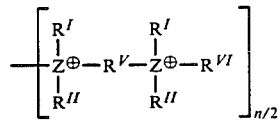 (VI)

in which n has the meaning given hereafter, Z represents nitrogen, phosphorus or arsenic, $R^I$, $R^{II}$, $R^{III}$ and $R^{IV}$, which are identical or different, represent hydrogen, an alkyl, an aryl or arylalkyl radical containing 1 to 12 atoms, whereby $R^{IV}$ may also represent a bivalent alkylene radical containing 4 to 6 carbon atoms and two or three atoms of $R^I$, $R^{II}$, $R^{III}$ and $R^{IV}$ may also be joined with one or two nitrogen atoms to form a di-lower alkyl piperidinium group, a lower alkyl pyridinium group or a di-lower alkyltriethylene diammonium group;
- $R^V$ and $R^{VI}$, which are identical or different, represent a lower alkylene, lower cycloalkylene or phenylene di-lower alkylene radical;
- p is an integer which is equal to 1 to 3 inclusive, and
- n, represents the oxidation number of the metal or the number of ammonium, phosphonium or arsonium functions present in the Q group and is equal to 1 to 40.

2. A 1,3,5-oxadiazine-2,4,6-trione salt according to claim 1, in which in the formula I;
- p is equal to 1;
- R represents a $C_1$-$C_{17}$ alkyl, $C_2$-$C_{18}$ alkenyl, cyclohexyl or benzyl radical;
- Q has the meaning in claim 1, and
- n is equal to 1 or 2.

3. A 1,3,5-oxadiazine-2,4,6-trione salt according to claim 1, in which in the formula I:
- p is equal to 2;
- R represents a $C_6$-alkylene, $C_4$-alkenylene, $C_4$-$C_6$ cycloalkylene or phenylene di-methylene radical;
- Q has the meaning in claim 1, and
- n is equal to 1 or 2.

4. An asymmetrical molecular 1,3,5-oxadiazine-2,4,6-trione having the following formula:

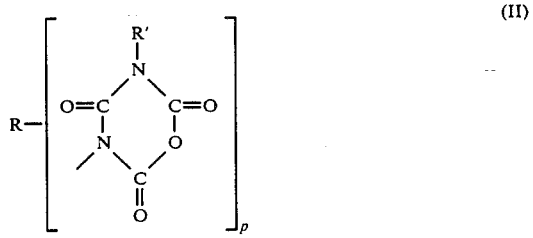 (II)

in which
- R represents a monovalent, divalent or trivalent alkyl, alkylene, cycloalkyl or arylalkyl radical containing at most 18 carbon atoms;
- p is an integer equal to 1 to 3 inclusive, and
- R' which is different from R, is hydrogen, a halogen atom, a $C_1$-$C_6$ alkyl radical which can be substituted by a chlorine atom, a $C_3$-$C_4$ alkenyl radical which can be substituted by a chlorine atom, a cyclohexyl radical, a benzyl radical which can be substituted by a $CF_3$, $CH_2Cl$ or $NO_2$ group, a $C_2$-$C_8$ acyl radical, a p-arylsulfonyl radical or a lower alkoxy carbonyl methylene radical.

5. An asymmetrical molecular 1,3,5-oxadiazine 2,4,6-trione according to claim 4 in which in the formula II:
- p and R have the meanings given in claim 4 and R' which is different from R is hydrogen, a halogen atom, a $C_1$-$C_6$ alkyl radical which can be substituted by a chlorine atom, a $C_3$-$C_4$ alkenyl radical which can be substituted by a chlorine atom, a cyclohexyl radical, a benzyl radical which can be substituted by a $CF_3$, $CH_2Cl$ or $NO_2$ group or a $C_2$-$C_8$ acyl radical selected among the acetyl, oxalyl, phthalyl and benzoyl radicals, a p-toluene sulfonyl radical or an ethoxy carbonyl methylene radical.

6. An asymmetrical molecular 1,3,5-oxadiazine-2,4,6-trione according to claim 4, in which in the formula II:
- p is equal to 1;
- R represents a $C_1$-$C_{17}$ alkyl, $C_2$-$C_{18}$ alkenyl, cyclohexyl or benzyl radical, and
- R' which is different from R, has the meaning given in claim 4.

7. An asymmetrical molecular 1,3,5-oxadiazine-2,4,6-trione according to claim 4, in which in the formula II:
- p is euqal to 2;
- R represents a $C_6$-alkylene, $C_4$-alkenylene, $C_4$-$C_6$ cycloalkylene or phenylene di-methylene radical and,
- R', which is different from R, has the meaning given in claim 4.

8. An asymmetrical molecular 1,3,5-oxadiazine-2,4,6-trione according to claim 4, in which in the formula II:
- p is equal to 1;
- R represents a $C_1$-$C_{17}$ alkyl, $C_2$-$C_{18}$ alkenyl, cyclohexyl or benzyl radical, and
- R' which is different from R, is hydrogen, a halogen atom, a $C_1$-$C_6$ alkyl radical which can be substituted by a chlorine atom, a $C_3$-$C_4$ alkenyl radical which can be substituted by a chlorine atom, a cyclohexyl radical, a benzyl radical which can be substituted by a $CF_3$, $CH_2Cl$ or $NO_2$ group, a $C_2$-$C_8$ acyl radical selected from the group consisting of acetyl, oxalyl, phthalyl and benzoyl radicals, a p-toluene sulfonyl radical or an ethoxycarbonyl methylene radical.

9. An asymmetrical molecular 1,3,5-oxadiazine-2,4,6-trione according to claim 4, in which in the formula II:
p is equal to 2;
R represents a $C_6$-alkylene, $C_4$-alkenylene, $C_4$–$C_6$ cycloalkylene or phenylene di-methylene radical, and
R', which is different from R, is hydrogen, a halogen atom, a $C_1$–$C_6$ alkyl radical which can be substituted by a chlorine atom, a $C_3$–$C_4$ alkenyl radical which can be substituted by a chlorine atom, a cyclohexyl radical, a benzyl radical which can be substituted by a $CF_3$, $CH_2Cl$ or $NO_2$ group, a $C_2$–$C_8$ acyl radical selected among the acetyl, oxalyl, phthalyl and benzoyl radicals, a p-toluenesulfonyl radical or an ethoxy carbonyl methylene radical.

10. A process for preparing a salt of a 1,3,5-oxadiazine-2,4,6-trione having the formula I according to claim 1, in which an organic isocyanate of the following formula III:

$$R(NCO)_p \qquad (III)$$

in which R and p have the meanings given in claim 1, is reacted with a cyanate salt of the formula:

$$Q(NCO)_n \qquad (IV)$$

in which Q and n have the meanings given in claim 1 and with carbon dioxide.

11. A process for preparing a salt of a 1,3,5-oxadiazine-2,4,6-trione according to claim 2, in which an organic isocyanate of the following formula III:

$$R(NCO)_p \qquad (III)$$

in which R and p have the meanings given in claim 2, is reacted with a cyanate salt of the formula:

$$Q(NCO)_n \qquad (IV)$$

in which Q and n have the meanings given in claim 2 and with carbon dioxide.

12. A process for preparing a salt of a 1,3,5-oxadiazine-2,4,6-trione according to claim 3, in which an organic isocyanate of the following formula (III):

$$R(NCO)_p \qquad (III)$$

in which R and p have the meanings given in claim 3, is reacted with a cyanate salt of the formula:

$$Q(NCO)_n \qquad (IV)$$

in which Q and n have the meanings given in claim 3 and with carbon dioxide.

13. A process according to claim 10, in which the organic isocyanate of the formula:

$$R(NCO)_p \qquad (III)$$

in which R and p have the meanings as in claim 1, is prepared in situ by reacting a cyanate salt of the formula:

$$Q(NCO)_n \qquad (IV)$$

in which Q has the meanings given in claim 1, and n is an integer equal to 1 or 2, with an organic halide or sulfate of the formula:

$$RX_p \qquad (XIII)$$

in which R and p have the meanings given in claim 1, and X represents a halogen or a sulfate, an alkylsulfate or arylsulfonyl radical, possibly in the presence of a catalyst.

14. A process according to claim 13, in which an organic halide or sulfate of the formula:

$$RX_p \qquad (XIII)$$

in which R, p and X have the meanings given in claim 13, is reacted with a cyanate salt of the formula:

$$Q(NCO)_n \qquad (IV)$$

in which Q and n have the meanings given in claim 13 and with carbon dioxide.

15. A process according to claim 10, in which the organic isocyanate of the formula $R(NCO)_p$ is one member selected from the group consisting of methyl isocyanate, ethyl isocyanate, 1-isocyanatobutane, 1-isocyanatodecane, allyl isocyanate, 1-isocyanato-octadec-9-ene, hexamethylene diisocyanate, 1,4-diisocyanatobut-2-ene, vinyl isocyanate, isopropyl isocyanate, 2,5-diisocyanatohexane, isocyanato-isoheptadecane, t-butyl isocyanate, 5-methyl-2,5,8-triisocyanatononane, cyclohexyl isocyanate, 1,3-diisocyanatocyclobutane, 1,4-diisocyanatocyclohexane, benzyl isocyanate, α,α'-diisocyanato-p-xylene and mixtures thereof.

16. A process according to claim 10, in which a cyanate salt of the formula:

$$Q(NCO)_n \qquad (IV)$$

in which n is equal to 1 or 2 and Q represents an alkaline or alkaline-earth metal is used.

17. A process according to claim 16, in which the metal is sodium or potassium.

18. A process according to claim 10, in which the cyanate salt is one member selected from the group consisting of tetramethylammonium cyanate, tetraethylammonium cyanate, tetrapropylammonium cyanate, tetrabutylammonium cyanate, tetraamylammonium cyanate, tetrahexylammonium cyanate, tributylmethylammonium cyanate, tricaprylmethylammonium cyanate, dodecyltrimethylammonium cyanate, benzyltrimethylammonium cyanate, benzyltriethylammonium cyanate, benzyltributylammonium cyanate, benzylisopropyldimethylammonium cyanate, benzyltripropylammonium cyanate, phenyltrimethylammonium cyanate, phenyltriethylammonium cyanate, methyltributylphosphonium cyanate, tetrabutylphosphonium cyanate, tetraphenylphosphonium cyanate, benzyltriethylarsonium cyanate, tetrapropylarsonium cyanate, tetraphenylarsonium cyanate, dimethylpiperidinium cyanate, methylpyridinium cyanate and mixtures of these compounds.

19. A process according to claim 10, in which the cyanate salt is one member selected from the group consisting of 1,4-bis(trimethylammonium)-butane cyanate, 1,6-bis(triethylammonium)hexane cyanate, 1,4-dimethyl-1,4-diaza-2,2,2-bicyclooctane cyanate, ionene of the formula:

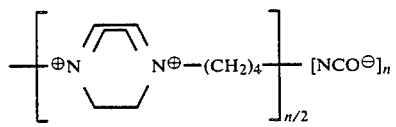

ionene of the formula:

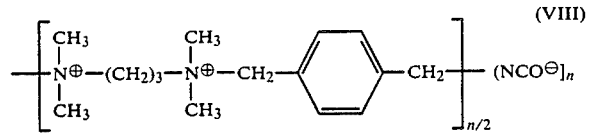

in which n is between 5 and 40, and mixtures of these compounds.

20. A process according to claim 10, in which the reaction takes place in the presence of an organic solvent which does not affect the reaction, at temperatures between about −80° C. and +250° C. and at pressures between about 0.2 bar and 150 bars.

21. A process according to claim 10, in which 0.5 to 2 equivalents of organic isocyanate are used per equivalent of cyanate salt.

22. A process according to claim 21, in which 0.8 to 1.2 equivalents or organic isocyanate are used per equivalent of cyanate salt.

23. A process according to claim 10, in which an amount of carbon dioxide between 0.1 and 20 moles per equivalent of cyanate salt is used.

24. A process according to claim 23, in which an amount of carbon dioxide between 0.8 and 2 moles per equivalent of cyanate salt is used.

25. A process according to claim 20, in which the solvent is one member selected from the group consisting of carbon tetrachloride, chloroform, dichloromethane, 1,2-dichloroethane, 1,1-dichloroethane, mixtures of cis and trans isomers of 1,2-dichloroethylene, o-dichlorobenzene, dioxane, ethyl acetate, dimethoxyethane, tetrahydrofurane, toluene, α-methylnaphthalene, acetone, methylethylketone, acetonitrile, propionitrile, benzonitrile, benzyl cyanide, nitrobenzene, nitrotoluene, dimethylformamide, dimethylacetamide, tetramethylurea, N-methylpyrrolidone, hexamethylphosphotriamide, dimethyl sulfoxide, and mixtures of at least two of these solvents, the solvents being preferably one member selected from the group consisting of chlorinated hydrocarbons, linear or cylic ethers, ketones and nitrides.

26. A process for preparing a molecular 1,3,5-oxadiazine-2,4,6-trione, in which a salt of 1,3,5-oxadiazine-2,4,6-trione according to claim 1 is reacted with a reagent of the following formula:

R'Y    (IX)

in which R' is hydrogen, a halogen atom, a $C_1$–$C_6$ alkyl radical which can be substituted by a chlorine atom, a $C_3$–$C_4$ alkenyl radical which can be substituted by a chlorine atom, a cyclohexyl radical, a benzyl radical which can be substituted by a $CF_3$, $CH_2Cl$ or $NO_2$ group, a $C_2$–$C_8$ acyl radical, a p-aryl sulfonyl radical or a lower alkoxy carbonyl methylene radical and Y represents a halogen, a sulfate radical or the rest of a mineral or organic acid.

27. A process according to claim 26, in which the reagent of the formula R'Y is one member selected from the group consisting of mineral and organic acids which are capable of donating a proton to the salts of 1,3,5-oxadiazines-2,4,6-triones of the formula (I) which have basic properties.

28. A process according to claim 26, in which the acid is one member selected from the group consisting of hydrochloric acid, sulfuric acid, acetic acid, benzoic acid, formic acid and oxalic acid.

29. A process according to claim 26, in which the reagent of the formula R'Y is an organic halide or sulfate containing 1 to 8 carbon atoms.

30. A process according to claim 26, in which the reagent of the formula R'Y is one member selected from the group consisting of dimethyl sulfate, diethyl sulfate, benzyl chloride, allyl chloride, 1-chloro-but-2-ene, cyclohexyl chloride, methyl chloride, methyl iodide, α-chloro-p-nitrotoluene, 1-chlorohexane, α-chloro-p-trifluoro-methyltoluene, acetyl chloride, benzoyl chloride, p-toluenesulfonyl chloride, oxalyl chloride, phthalyl chlorides, 1,4-dichlorobutene, α,α'-dichloro-m-xylene, α,α'-dichloro-p-xylene, 1,6-dichlorohexane and mixtures of these compounds.

31. A process according to claim 26, in which a molecular 1,3,5-oxadiazine-2,4,6-trione is prepared by reacting an organic isocyanate of the formula:

R(NCO)$_p$    (III)

in which R and p have the meanings given in claim 1, with a cyanate salt of the formula:

Q(NCO)$_n$    (IV)

in which Q and n have the meanings given in claim 1, with carbon dioxide and with a reagent of the formula:

R'Y    (IX)

in which R' and Y have the meanings given in claim 26.

32. A process according to claim 26, in which a molecular 1,3,5-oxadiazine-2,4,6-trione is prepared by reacting an organic isocyanate of the formula:

R(NCO)$_p$    (III)

in which R and p have the meanings given in claim 2, with a cyanate salt of the formula:

Q(NCO)$_n$    (IV)

in which Q and n have the meanings given in claim 2, with carbon dioxide and with a reagent of the formula:

R'Y    (IX)

in which R' and Y have the meanings given in claim 26.

33. A process according to claim 26, in which a molecular 1,3,5-oxadiazine-2,4,6-trione is prepared by reacting an organic isocyanate of the formula:

R(NCO)$_p$    (III)

in which R and p have the meanings given in claim 3, with a cyanate salt of the formula:

Q(NCO)$_n$    (IV)

in which Q and n have the meanings given in claim 3, with carbon dioxide and with a reagent of the formula:

R'Y    (IX)

in which R' and Y have the meanings given in claim 26.

* * * * *